United States Patent [19]

Wachs

[11] Patent Number: 6,084,135
[45] Date of Patent: *Jul. 4, 2000

[54] PRODUCTION OF FORMALDEHYDE USING CARBON OXIDES, HYDROGEN AND H$_2$S

[75] Inventor: Israel E. Wachs, Bridgewater, N.J.

[73] Assignee: Lehigh University, Bethlehem, Pa.

[*] Notice: This patent is subject to a terminal disclaimer.

[21] Appl. No.: 09/216,843

[22] Filed: Dec. 21, 1998

Related U.S. Application Data

[60] Provisional application No. 60/070,113, Dec. 31, 1997.

[51] Int. Cl.$^7$ .......................... C07C 45/00; C07C 319/00
[52] U.S. Cl. ............................................. 568/482; 568/70
[58] Field of Search ....................................... 568/482, 70

[56] References Cited

U.S. PATENT DOCUMENTS

| | | |
|---|---|---|
| 3,070,632 | 12/1962 | Olin et al. . |
| 4,410,931 | 10/1983 | Buchholz . |
| 4,449,006 | 5/1984 | Haines . |
| 4,536,492 | 8/1985 | Haines . |
| 4,544,649 | 10/1985 | Wachs et al. . |
| 4,570,020 | 2/1986 | Ratcliff et al. . |
| 4,665,242 | 5/1987 | Boulinguiez et al. . |

FOREIGN PATENT DOCUMENTS

| | | |
|---|---|---|
| 0 068 377 | 1/1983 | European Pat. Off. . |
| 0 104 507 | 4/1984 | European Pat. Off. . |
| 0 267 711 | 5/1988 | European Pat. Off. . |
| 212993 | of 0000 | Russian Federation . |
| 8 002 177 | 9/1981 | Sweden . |
| 589292 | 6/1947 | United Kingdom . |
| 1263139 | 2/1972 | United Kingdom . |
| 2238486 | 6/1991 | United Kingdom . |
| WO 98/17618 | 4/1998 | WIPO . |

OTHER PUBLICATIONS

Turk, et al., "Ammonia Injection Enhances Capacity of Activated Carbon for Hydrogen Sulfied and Methyl Mercaptan," Enviro. Sci. Technol., vol. 23, No. 10, 1242–1245, 1989.

Weigand, et al., "The Local Structure of Absorbed Methyl Thiolate: The Reactions of Methanethiol on Mo(110)," Surface Science, vol. 279, 105–112, 1992.

Bol and Friend, "The Effects of Oxygen on Selectivity: The Reactions of 2–Propanethiolate on Oxygen–Covered Rh(111)," J. Am. Chem. Soc., vol. 117, 5351–5358, 1995.

Bosch, et al., "Formation and Control of Nitrogen Oxides," Catalysis Today, vol. 2, No. 4, 369–379, 1988.

Busca, et al., "Mechanism of Selective Methanol Oxidation Over Vanadium Oxide–Titanium Oxide Catalysts: A FT–IR and Flow Reactor Study," J. Phys. Chem., vol. 91, 5263–5269, 1987.

Herman, et al., "Development of Active Oxide Catalysts for the Direct Oxidation of Methane to Formadehyde," Catalysis Today, vol. 37, 1–14, 1997.

Jehng, et al., "Surface Modified Niobium Oxide Catalyst: Synthesis, Characterization, and Catalysis," Applied Catalysis A, vol. 83, 179–200, 1992.

Kim and Wachs, "Surface Chemistry of Supported Chromium Oxide Catalysts," Journal of Catalysis, vol. 142, 166–171, 1993.

Jehng and Wachs, "Molecular Design of Supported Niobium Oxide Catalysts," Catalysis Today, vol. 16, 417–426, 1993.

Kim and Wachs, "Surface Rhenium Oxide–Support Interaction for Supported Re$_2$O$_7$ Catalysts," Journal of Catalysis, vol. 141, 419–429, 1993.

Deo, et al., "Physical and Chemical Characterization of Surface Vanadium Oxide Supported on Titania: Influence of Titania Phase (Anatase, Rutile, Brookite and B)," Applied Catalysis A, vol. 91, 27–42, 1992.

Deo and Wachs, "Reactivity of Supported Vanadium Oxide Catalysts: The Partial Oxidation of Methanol," Journal of Catalysis, vol. 146, 323–334, 1994.

Deo and Wachs, "Effect of Additives on the Structure and Reactivity of the Surface Vanadium Oxide Phase in V$_2$O$_5$/TiO$_2$ Catalysts," Journal of Catalysis, vol. 146, 335–345, 1994.

Jehng, et al., "Surface Chemistry of Silica–Titania–Supported Chromium Oxide Catalysts," J. Chem. Soc. Faraday Trans., vol. 91(5), 953–961, 1995.

Kim, et al., "Molecular Structures and Reactivity of Supported Molybdenum Oxide Catalysts", Journal of Catalysis, vol. 146, 268–277, 1994.

Banares, et al., "Molybdena on Silica Catalysts: Role of Preparation Methods of the Structure–Selectivity Properties for the Oxidation of Methanol," Journal of Catalysis, vol. 150, 407–420, 1994.

Jehng and Wachs, "The Molecular Structures and Reactivity of V$_2$O$_5$/TiO$_2$/SiO$_2$ Catalysts," Catalyst Letters, vol. 13, 9–20, 1992.

Sun, et al., "Partial Oxidation of Methane by Molecular Oxygen Over Supported V$_2$O$_5$ Catalysts: A Catalytic abd in situ Raman Spectroscopy Study," Methane and Alkane Conversion Chemistry, 219–226, 1995.

(List continued on next page.)

*Primary Examiner*—Paul J. Killos
*Assistant Examiner*—J. Parsa
*Attorney, Agent, or Firm*—Banner & Witcoff, Ltd.

[57] ABSTRACT

A method wherein a gas stream containing hydrogen, a carbon oxide and hydrogen sulfide is first passed in contact with a catalyst comprising a porous alumina supported sulfided metal selected from the group consisting of molybdenum (Mo), chromium (Cr), tungsten (W), manganese (Mn), nickel (Ni), iron (Fe), zinc (Zn), cobalt (Co), copper (Cu), tin (Sn), vanadium (Va) and mixtures thereof, optionally promoted by an alkali metal sulfide, to convert said hydrogen, carbon oxide and hydrogen sulfide to methyl mercaptans, (primarily methanethiol (CH$_3$SH)), and the gas stream containing the methyl mercaptans are passed in contact with a catalyst comprising a supported metal oxide or a bulk metal oxide in the presence of an oxidizing agent and for a time sufficient to convert at least a portion of the methyl mercaptan to formaldehyde (CH$_2$O), and sulfur dioxide (SO$_2$).

11 Claims, 2 Drawing Sheets

OTHER PUBLICATIONS

Sun, et al., In Situ Raman Spectroscopy during the Partial Oxidation of Methane to Formaldehyde over Supported Vanmadium Oxide Catalysts, J. of Catalysis, vol. 165, 91–101, 1997.

Arora, et al., "Surface Aspects of Bismuth—Metal Oxide Catalysts", Journal of Catalysis, vol. 159, 1–13, 1996.

Baiker, et al., "Influence of the A–Site Cation in $AcoO_3$ (A=La, Pr, Nd and Gd) Perovskite–Type Oxides on Catalytic Activity for Methane Combustion," Journal of Catalysis. vol. 146, 268–277, 1994.

Hardcastle, et al., "Determination of Molybdenum–Oxygen Bond Distances and Bond Orders by Raman Spectroscopy," J. Raman Spectroscopy, 21, 683–691, 1990.

Hardcastle, et al., "Determination of Vanadium–Oxygen Bond Distances and Bond Orders by Raman Spectroscopy," J. Physical Chemistry, 95(13) 5031–5041, 1991.

Hardcastle, "Determination of the Molecular Structures of Tungstates by Raman Spectroscopy," J. Raman Spectroscopy, 26, 397–405, 1995.

Weckhuysen, et al., "Raman Spectroscopy of Suported Chromium Oxide Catalysts Determination of Chromium—Oxygen Bond Distances and Bond Orders," J. Chem. Soc. Faraday Trans., 92(11), 1969–1973, 1996.

Hardcastle, et al., "Determination of Niobium–Oxygen Bond Distances and Bond Orders by Raman Spectroscopy," Solid State Ionics, 45, 201–213, 1991.

Chemical Abstracts, 089(17), Abstr. No. 146366, "Possible Utilization of Dimethyl Ether".

Chemical Abstracts, 114(8), Abstr. No. 114(8), Abstr. No. 066367, "Photooxidation of Dimethyl Sulfide and Dimethy Disulfide. II: Mechanism Evaluation".

Yin, et al., "Photooxidation of Dimethyl Sulfide and Dimethyl Disulfide. II: Mechanism Evaluation," J. Atmos. Chem., vol. 11, No. 4, 365–399, Cal. Inst. Tech., Dept of Chem. Eng., Pasadena, 1990.

Mater. Vses. Konf., "Probl. Povysh. Urovnya Ispol'Z. Vtorichnykh Mater. Resur. Khim. Prom–Sti.," (38YXAG); 76, 105–111, Lenigr. Tekh. Inst., Lenigard, USSR.

International Search Report for PCT/US98/27411 dated Mar. 29, 1999.

Applied Catalysis, 33:309–330 (1987).

PRODUCTION OF FORMALDEHYDE USING CARBON OXIDES, HYDROGEN AND $H_2S$

This application claims the benefit under 35 U.S.C. 119 (e)(1) of prior filed provisional application 60/070,113 filed Dec. 31, 1997.

BACKGROUND OF THE INVENTION

1. Field of the Invention

This invention broadly relates to a process for producing formaldehyde from a gas stream containing a mixture of hydrogen, hydrogen sulfide ($H_2S$) and a carbon oxide, wherein the carbon oxide is selected from carbon monoxide (CO), carbon dioxide ($CO_2$) and mixtures thereof More particularly, this invention provides a method wherein hydrogen, a carbon oxide and hydrogen sulfide are first passed in contact with a catalyst comprising a porous alumina supported sulfided metal selected from the group consisting of molybdenum (Mo), chromium (Cr), tungsten (W), manganese (Mn), nickel (Ni), iron (Fe), zinc (Zn), cobalt (Co), copper (Cu), tin (Sn), vanadium (V) and mixtures thereof, optionally promoted by an alkali metal sulfide, to convert said hydrogen, carbon oxide and hydrogen sulfide to methyl mercaptans, (primarily methanethiol ($CH_3SH$)), and the methyl mercaptans are then passed in contact with a catalyst comprising certain supported metal oxides or certain bulk metal oxides in the presence of an oxidizing agent and for a time sufficient to convert at least a portion of the methyl mercaptans to formaldehyde ($CH_2O$) and sulfur dioxide ($SO_2$).

2. Description of Related Art

Olin et al., U.S. Pat. No. 3,070,632 describes a catalytic process for producing methanethiol ($CH_3SH$) from a gaseous feed comprising a mixture of hydrogen, carbon monoxide (CO) and hydrogen sulfide ($H_2S$). Gases containing $H_2S$ are often considered an unwanted waste stream. According to the patent, the gaseous mixture (preferably containing a stoichiometric excess of hydrogen and hydrogen sulfide) is contacted, at a temperature of at least about 100° to 400° C. and at a super-atmospheric pressure, with a sulfactive catalyst comprising a metal sulfide of a metal selected from the group consisting of molybdenum (Mo), chromium (Cr), tungsten (W), manganese (Mn), nickel (Ni), iron (Fe), zinc (Zn), cobalt (Co), copper (Cu), tin (Sn), vanadium (V) and mixtures thereof. The gas and catalyst are contacted at a space velocity from about 150 to 1500 liters of gas at standard temperature and pressure per liter of catalyst per hour. Promoters such as organic amines, may optionally be used.

Buchholz, U.S. Pat. No. 4,410,731; Haines, U.S. Pat. No. 4,449,006 and 4,536,492 and Barrault et al., Applied Catalysis, 33:309–330 (1987) also describe catalytic processes for producing methanethiol ($CH_3SH$) from a mixture of hydrogen, carbon monoxide (CO) and hydrogen sulfide ($H_2S$) (or elemental sulfur). According to these patents and the article, the mixture is contacted, at an elevated temperature and pressure, with a porous alumina supported sulfactive catalyst comprising a mixture of a sulfided metal selected from the group consisting of molybdenum (Mo), chromium (Cr), manganese (Mn), nickel (Ni), iron (Fe), zinc (Zn), cobalt (Co), tungsten (W), vanadium (V) and mixtures thereof, and an alkali metal sulfide. Boulinguiez et al., U.S. Pat. No. 4,665,242, describes a similar catalytic process characterized by the added step of removing water from the unreacted, recycle gases before returning them to the catalytic reactor.

The art has also identified methyl mercaptans, such as methanethiol ($CH_3SH$) and dimethyl sulfide ($CH_3SCH_3$), as hazardous pollutants, and has suggested a variety of ways for their destruction. Noncatalytic gas phase oxidation of such reduced sulfur compounds has been shown to produce primarily sulfur oxide and carbon oxide products. A. Turk et al., Envir. Sci. Technol 23:1242–1245 (1989). Investigators have observed that oxidation of methanethiol ($CH_3SH$) and ethanethiol ($CH_3CH_2SH$) in the presence of single crystal metal surfaces (Mo, Ni, Fe, Cu) results in the formation of methane and ethane, nonselective decomposition to atomic carbon, gaseous hydrogen and the deposition of atomic sulfur on the metal surface via a stoichiometric reaction (See Wiegand et al., Surface Science, 279(1992): 105–112). Oxidation of higher mercaptans, e.g., propanethiol on oxygen-covered single crystal metal surfaces (Rh), produced acetone via a stoichiometric reaction at low selectivity and accompanied by sulfur deposition on the metal surface (See Bol et al., J. Am. Chem. Soc., 117(1995): 5351–5258). The deposition of sulfur on the metal surface obviously precludes continuous operation.

The art also has disclosed using catalysts comprising a two-dimensional metal oxide overlayer on titania and silica supports, e.g., vanadia on titania, for catalytically reducing $NO_x$ by ammonia to $N_2$ and $H_2O$ in the presence of sulfur oxides. Bosch et al., Catal. Today 2:369 et seq. (1988). Thus, such catalysts are known to be resistant to poisoning by sulfur oxides. It also is known that such catalysts, as well as certain bulk metal oxides catalysts, can be used to oxidize methanol to formaldehyde selectively. Busca et al, J. Phys. Chem. 91:5263 et seq. (1987).

Applicant recently made the discovery that a supported metal oxide catalyst can be used to oxidize methyl mercaptans, such as methanethiol ($CH_3SH$) and dimethyl sulfide ($CH_3SCH_3$), selectively to formaldehyde in a continuous, heterogenous catalytic process without being poisoned by the reduced sulfur. On the basis of that discovery, applicant has envisioned the present process as a way of converting gaseous streams containing hydrogen, a carbon oxide and hydrogen sulfide to formaldehyde.

BRIEF DESCRIPTION OF THE INVENTION

Figure 1:
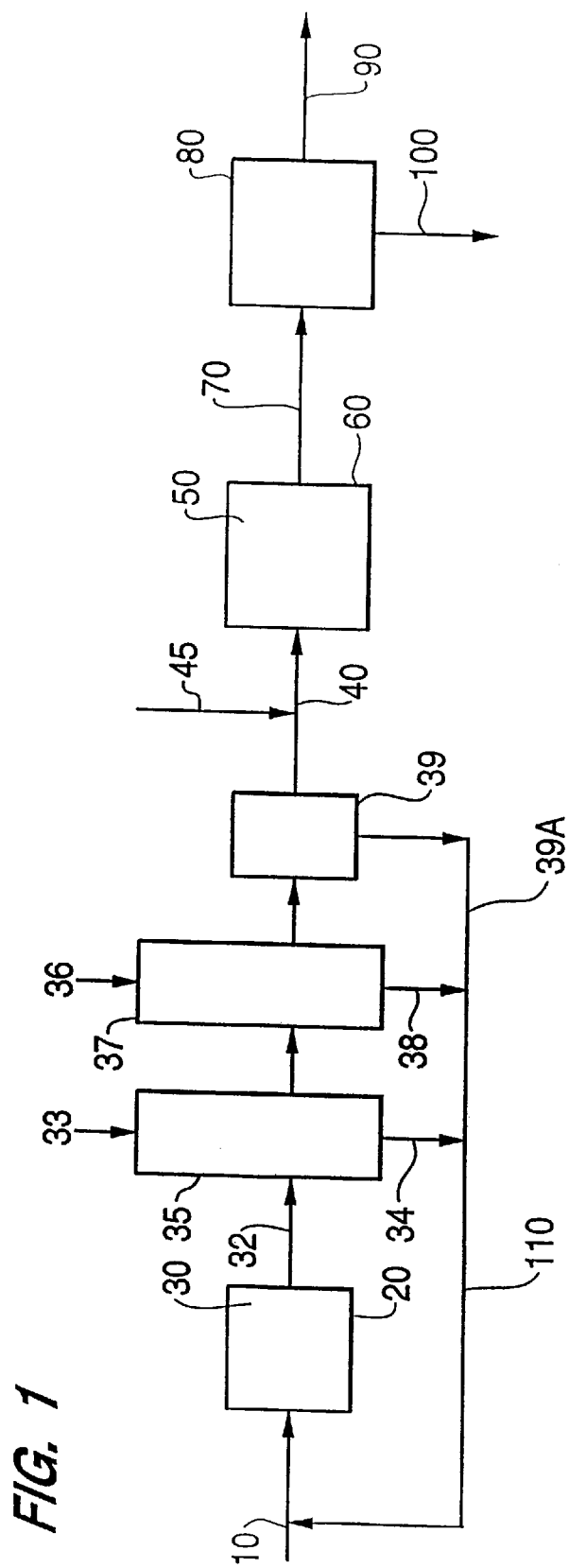
FIG. 1 is a schematic drawing of a process of the present invention.
Figure 2:
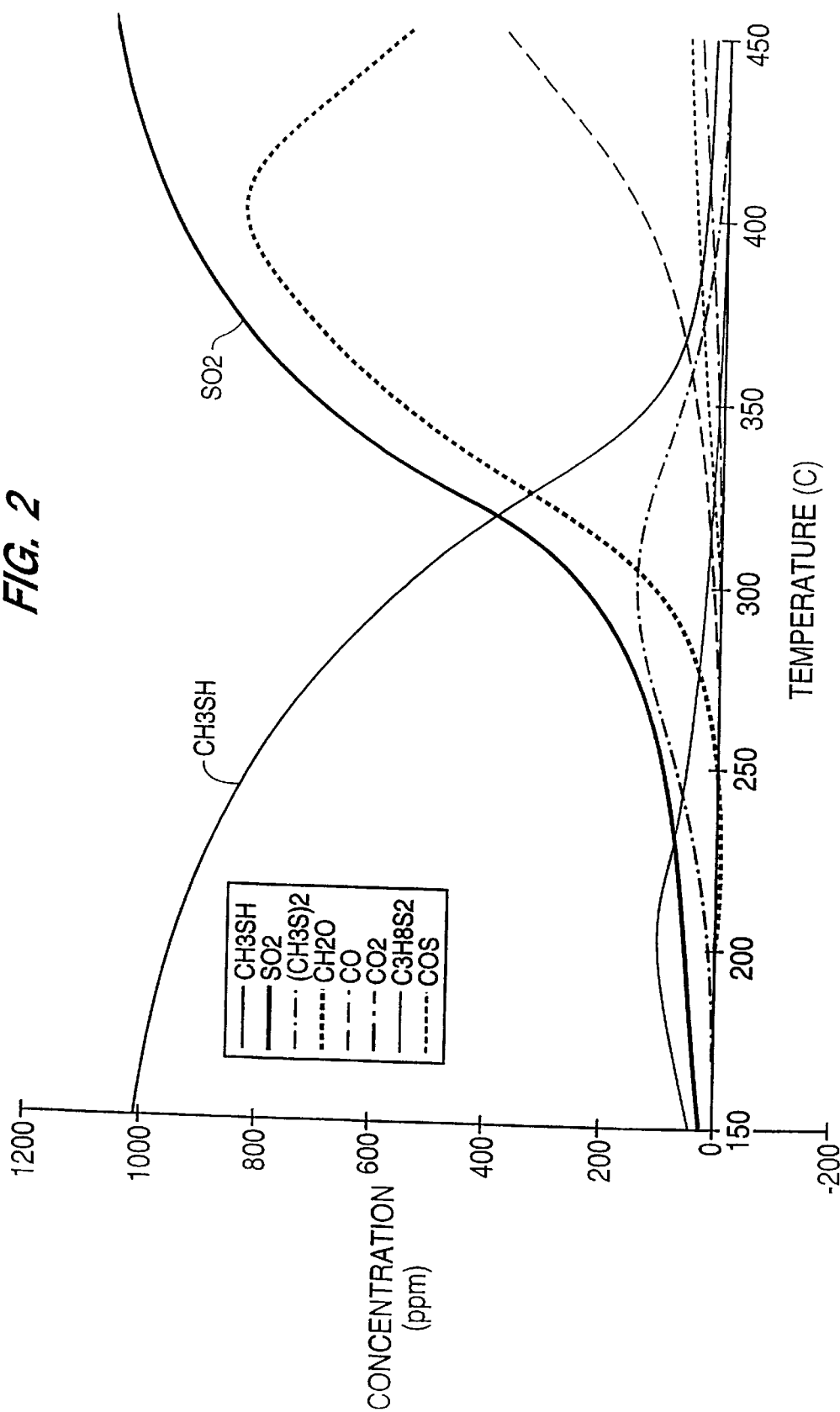
FIG. 2 illustrates the distribution of products produced by oxidizing methanethiol over a vanadia on titania catalyst containing about 1% by weight vanadia over the temperature range of 150° to 450° C. Maximum selectivity for the conversion of methanethiol to formaldehyde was observed at a temperature of about 400° C. Starting at about 300° C., there was a significant conversion of methanethiol to formaldehyde.

The present invention provides a process for producing formaldehyde from a gas stream containing a mixture of hydrogen ($H_2$), carbon oxide (CO and/or $CO_2$) and hydrogen sulfide ($H_2S$). As used throughout the specification and claims, the term "carbon oxide" is intended to embrace carbon monoxide (CO), carbon dioxide ($CO_2$) and mixtures thereof Generally, the gas stream may contain a sizable fraction of both carbon monoxide (CO) and carbon dioxide ($CO_2$). Also as used through out the specification and claims the term "hydrogen sulfide" is intended not only to embrace $H_2S$ directly, but also is intended to include elemental sulfur that is converted to $H_2S$ by reaction with hydrogen, such reaction possibly occurring prior to or simultaneously with the reactions leading to the formation of methyl mercaptans. The terms "sufided," "sulfactive" and similar terms describe a procedure whereby an alumina supported metal oxide catalyst is treated with hydrogen sulfide or vaporous elemental sulfur, in the presence of hydrogen, at an elevated temperature for a time sufficient to activate the catalyst, i.e., produce a catalyst active for catalyzing the reaction of a mixture of hydrogen, a carbon oxide and hydrogen sulfide to methyl mercaptan.

More particularly, this invention provides a method wherein a gas stream containing hydrogen, a carbon oxide and hydrogen sulfide ($H_2S$) is first passed in contact with a catalyst comprising a porous alumina supported sulfided metal oxide of a metal selected from the group consisting of molybdenum (Mo), chromium (Cr), tungsten (W), manganese (Mn), nickel (Ni), iron (Fe), zinc (Zn), cobalt (Co), copper (Cu), tin (Sn), vanadium (V) and mixtures thereof, optionally promoted by an alkali metal sulfide, to convert said hydrogen, carbon monoxide and hydrogen sulfide to methyl mercaptans, (e.g., methanethiol ($CH_3SH$)), and the methyl mercaptans are then passed in contact with a catalyst comprising certain supported metal oxides or certain bulk metal oxides in the presence of an oxidizing agent and for a time sufficient to convert at least a portion of the methyl mercaptans to formaldehyde ($CH_2O$) and sulfur dioxide ($SO_2$). Preferably, the metal of the porous alumina supported sulfided metal oxide is selected from oxides of molybdenum (Mo), chromium (Cr), manganese (Mn), nickel (Ni), iron (Fe), zinc (Zn), cobalt (Co), copper (Cu), tin (Sn), tungsten (W), vanadium (V) and mixtures thereof, preferably promoted by an alkali metal sulfide. For example, a suitable sulfided catalyst can be prepared by sulfiding a composition consisting essentially of tungsten oxide promoted with potassium on alumina (hereafter referred to as a W—K—$Al_2O_3$ catalyst).

The process involves flowing the gaseous stream containing hydrogen, carbon oxide and hydrogen sulfide ($H_2S$) in contact with a catalyst comprising a porous alumina supported sulfided metal oxide of a metal broadly selected from the group consisting of molybdenum (Mo), chromium (Cr), tungsten (W), manganese (Mn), nickel (Ni), iron (Fe), zinc (Zn), cobalt (Co), copper (Cu), tin (Sn), vanadium (V) and mixtures thereof, optionally promoted by an alkali metal sulfide. The gaseous mixture is contacted with the catalyst at a temperature of at least about 200° C. for a time sufficient to convert at least a portion of the $H_2$, CO and/or $CO_2$ and $H_2S$ to methyl mercaptan, primarily methanethiol. The gaseous stream containing the methyl mercaptan is thereafter contacted with a supported metal oxide or bulk metal oxide catalyst, under oxidizing conditions and for a time sufficient, to convert at least a portion of the methyl mercaptan to formaldehyde and sulfur dioxide. The formaldehyde then is recovered as a product separate from the residual gas stream.

In carrying out the process of the present invention, the metal oxide overlayer of the supported metal oxide used in the process of converting methyl mercaptan to formaldehyde is typically based on a metal selected from the group consisting of titanium (Ti), zirconium (Zr), molybdenum (Mo), rhenium (Re), vanadium (V), chromium (Cr), tungsten (W), manganese (Mn), niobium (Nb), tantalum (Ta) and mixtures thereof and the support generally is selected from titania, silica, zirconia, alumina, ceria, magnesia, niobia, lanthanum oxide, tin oxide and mixtures thereof. Generally, a support of titania, zirconia, ceria, niobia, tin oxide or their mixture is preferred. As a general rule, titanium (Ti), zirconium (Zr), niobium (Nb), tantalum (Ta) and tungsten (W) should not be used as the sole catalytic species with a silica support, nor should the support and the supported metal be the same. In the alternative embodiment of the present invention, the second step of the process, involving the conversion of methyl mercaptan to formaldehyde, can be carried out using a bulk metal oxide catalyst wherein the bulk metal oxides, and especially bulk mixed metal oxides, are based on molybdates (Mo), chromates (Cr), vanadates (V), rhenates (Re), titanates (Ti), niobates (Nb), tungstates (W), maganates (Mn) and mixtures thereof. Bulk metal catalysts based on molybdenum, chromium and vanadium are preferred.

The supported sulfided metal oxide catalyst compositions, the supported metal oxide catalyst compositions and the bulk metal oxide catalyst compositions useful for practicing the present invention are known in the prior art, as are their methods of production.

For the supported metal oxide catalyst used in the second step of the process, the preferred vanadium oxide may preferably be used in mixture with an oxide of one of molybdenum (Mo), tungsten (W), chromium (Cr), rhenium (Re), and manganese (Mn), supported on titania or silica. In the case of a vanadia on silica catalyst, an adjuvant selected from the group consisting of an oxide of titanium, zirconium, cerium, tin, niobium and tantalum, should generally be present to enhance catalytic activity. As noted above, vanadia on titania is particularly preferred as a metal oxide supported catalyst in the second step of the process.

DETAILED DESCRIPTION OF THE INVENTION

As noted, the present invention is directed to a method for selectively converting a gaseous mixture of hydrogen, a carbon oxide and $H_2S$ first to methyl mercaptans, such as methanethiol ($CH_3SH$), and then to formaldehyde and sulfur dioxide.

In accordance with the present invention, and with reference to FIG. 1, a gas stream 10 containing hydrogen, a carbon oxide, typically carbon monoxide (CO), and hydrogen sulfide ($H_2S$) is first passed in a reactor 20 in contact with a catalyst bed 30 comprising a porous alumina supported sulfided metal oxide of a metal selected from the group consisting of molybdenum (Mo), chromium (Cr), tungsten (W), manganese (Mn), nickel (Ni), iron (Fe), zinc (Zn), cobalt (Co), copper (Cu), tin (Sn), vanadium (V) and mixtures thereof, optionally promoted by an alkali metal sulfide. Preferably, the metal of the porous alumina supported sulfided metal oxide is selected from molybdenum (Mo), chromium (Cr), manganese (Mn), nickel (Ni), iron (Fe), zinc (Zn), cobalt (Co), tungsten (W), vanadium (V) and mixtures thereof, preferably promoted by an alkali metal sulfide. In one embodiment, the sulfided catalyst is a sulfided W—K—$Al_2O_3$ catalyst.

Any source for the hydrogen, hydrogen sulfide and carbon oxide raw materials can be used in the practice of the present invention. One convenient source for these materials is a facility for processing sour natural gas. The hydrogen sulfide may originate in a sour natural gas stream or, as noted above, may be produced from elemental sulfur and hydrogen prior to or simultaneously with the reactions producing the methyl mercaptan. The carbon oxides and hydrogen generally may be produced by steam reforming of methane (natural gas). It may also be desirable to pass the resulting synthesis gas through a water gas shift reaction to enrich its hydrogen and carbon monoxide contents. Carbon dioxide also may originate from a natural gas source.

In general, the ratio of carbon oxide to $H_2S$ to hydrogen in the gaseous feed used in the first step of the process of this invention is not narrowly critical. Preferably, the carbon oxide will be delivered to the reactor with a stoichiometric excess of both hydrogen sulfide (or sulfur) and hydrogen. Generally, the molar ratio of carbon oxide to $H_2S$ to hydrogen will typically range from about 1/3/2 to 1/8/8, most often a range of from 1/3/3 to 1/4/6 should be suitable. Based on experimental data reported in *Applied Catalysis*, 33:309–330 (1987) a 1/4/4 ratio for $CO_x/H_2S/H_2$ appears to be optimum for conversion and selectivity when using a sulfided W—K—$Al_2O_3$ catalyst.

The gas stream 10 containing hydrogen, a carbon oxide, typically carbon monoxide (CO), and hydrogen sulfide ($H_2S$) is contacted in reactor 20 in contact with the catalyst bed 30 at a temperature of at least 200° C., such as at a temperature of 250° to 400° C., and generally at a temperature between about 250° to 350° C. U.S. Pat. No. 4,570,020 suggests that methanethiol tends to encounter thermal instability at about 350° C. If this information is accurate, as the reaction temperature approaches and/or exceeds this temperature, one should take provisions to rapidly quench the so-formed methanethiol down to a temperature below about 350° C. in order to prevent thermal decomposition thereof. With regard to the space velocity of the feed gas, it is understood that longer contact times normally result in a greater amount of product. However, this may be offset by decomposition of methyl mercaptan product in contact with the catalyst, particularly at the higher temperatures.

The contacting is conducted for a time sufficient to convert said hydrogen, carbon oxide and hydrogen sulfide to methyl mercaptans, (e.g., methanethiol ($CH_3SH$)). The optimum reaction time (space velocity) varies with temperature, pressure and the molar ratio of the reactants. The space velocity will be maintained below about 4800 V/V/hr. As a general rule, higher conversions are associated with lower space velocities, e.g., a space velocity of 5 to 200 volume of gas (STP) per volume of catalyst per hour. In the broad practice of the invention, space velocities of up to 2000 volumes of gas (STP) per volume of catalyst per hour are generally contemplated.

While the reaction can be conducted over a wide range of pressures, the reactor 20 preferably is operated at a superatmospheric pressure, preferably at least about 12 atmospheres. An operating pressure up to 50 atmospheres is expected to be suitable, e.g., a pressure of 25–35 atmospheres is generally preferred. Because the reaction of CO and $H_2S$ is preferably conducted in the gas phase, the total reactor pressure should not result in a partial pressure of $H_2S$ that would cause the $H_2S$ to condense. Accordingly, unless it is desired in a specific circumstance that the reaction occur in the presence of both gaseous and liquid phases, the reactor conditions should be maintained to avoid $H_2S$ condensation.

The methyl mercaptan-containing gas stream 32 exiting reactor 20 may contain unreacted, hydrogen, carbon monoxide (CO) and $H_2S$ that would be needlessly oxidized further to water, $CO_2$ and $SO_2$, respectively, if permitted to proceed directly to the second reactor 60, where an oxygen containing gas is added to the inlet gas feed via line 45. The stream may also contain water. Therefore, unreacted hydrogen, carbon oxide (particularly CO) and $H_2S$ may be removed, preferably selectively, by various means known to those skilled in the art. For example, an absorption step 35 can be used to remove $H_2S$ by means of amine solutions 33, from which it can be recovered for recycle by a temperature controlled desorption (not shown) from line 34. Similarly, carbon oxides (especially CO) may be selectively absorbed in absorber 37, using specific absorbents introduced via line 36, recovered (by means not shown) and recycled via line 38. Hydrogen, which may contribute to an undesired temperature increase in a downstream catalytic reactor by virtue of its heat of combustion, may be removed through a selective permeable membrane 39 and recycled through line 39A. Water in gas stream 32 is preferably removed prior to processing the gas through additional catalytic reactors.

The residual gas thereafter contacts a supported metal oxide or a bulk metal oxide catalyst 50 in reactor 60 under oxidizing conditions at a temperature in the range of 200° to 700° C., preferably in the range of 300° to 600° C. and most often in the range of 325° to 500° C. The operating pressure for the catalytic reactor 60 is not critical. Operation at atmospheric pressure has been found suitable.

Air or an oxygen-enriched gas generally is added via stream 45 to establish oxidizing conditions in reactor 60. The selective oxidation produces formaldehyde and sulfur dioxide, which exits reactor 60 in stream 70. As noted, the oxidizing agent used in the selective methyl mercaptan oxidation can usually be oxygen or air. The contacting of the methyl mercaptan with the supported metal oxide catalyst or bulk metal oxide catalyst under an oxidizing atmosphere, e.g., in the presence of oxygen, and at an appropriate temperature, causes a selective conversion of the methyl mercaptan to formaldehyde.

The optimum reaction time in reaction zone 60 (space velocity) varies with temperature, pressure and the molar ratio of the reactants. The space velocity likely will be maintained below about 4800 V/V/hr. As a general rule, higher conversions are associated with lower space velocities, e.g., a space velocity of 5 to 200 volume of gas (STP) per volume of catalyst per hour. In the broad practice of the invention, space velocities of up to 2000 volumes of gas (STP) per volume of catalyst per hour are generally contemplated.

The preferred vanadia (vanadium oxide) on titania, supported metal oxide catalyst used in this step of the process has at least a portion, and preferably at least about 25 wt. %, of said supported vanadium oxide in a non-crystalline form.

Formaldehyde is the intended product of the present process and it can be recovered from the gaseous reaction products 70, separate from byproduct $SO_2$ and unreacted mercaptans 100, using any one of a number of ways known to those skilled in the art.

In particular, as will be recognized by those skilled in the art, the gases 70 leaving the reactor may contain unreacted starting products, including any inert gases that may have been added, as well as formaldehyde, sulfur dioxide and water. The principal by-products that are formed include carbon monoxide, which may be accompanied by carbon dioxide (often in a minor amount) and sulfur dioxide. COS may also be a minor product.

The reaction mixture leaving the second step reactor 70 is generally subject to further processing 80 in a conventional manner. For example, the formaldehyde product can be separated in a washer, or by indirect cooling, or also by fractional cooling. For example, the washing can be performed with water, in which case a multi-stage washer can be used. An aqueous formaldehyde solution 90 can be obtained in this manner separate from the sulfur dioxide. The sulfur dioxide can be disposed of by any technique known in the art. For example, the sulfur oxide (from stream 100) can be oxidized and converted to sulfuric acid. From the crude formaldehyde solution, commercial formaldehyde solutions can be prepared, such as by distillation for immediate technical use. The formaldehyde also can be condensed out of the reaction gas together with the water that has formed. In this manner, concentrated formaldehyde solutions in common commercial form can be obtained. Other ways for isolating the formaldehyde product will be apparent to those skilled in this art. The residual gas 100, possibly containing carbon monoxide may be treated (so as to recover sulfur oxides) and then recycled to the methyl mercaptan production step in reactor 20 (not shown).

For obtaining higher yields and selectivities in the conversion of methyl mercaptan to formaldehyde it may be desirable to conduct the reaction such that only a partial reaction takes place in a single pass through the reactor. For example, the pressure, temperature, composition of the starting gas mixture, the amount of catalyst and/or the rate of flow can be varied to cause a partial conversion of the mercaptan feed. The reactor effluent gas remaining after separation of the formaldehyde can then be recycled (not shown) into the reactor 60. It is desirable to add to this gas the amount of methyl mercaptan that has been consumed. In this manner, a continuous circulation can be achieved. If the gas is recirculated in this manner, the inert gases and the by-products, especially carbon monoxide and carbon dioxide, will concentrate in the recycled gas, and any excessive accumulation of these gases can be prevented by a continuous or discontinuous side-stream removal, which, as noted above, may be advantageously recycled to the first step of the process. It is also desirable to replace the removed exhaust gas with an equal amount of fresh gas.

The catalysts useful in the initial step of the process of this invention comprise a porous alumina supported sulfided metal oxide of a metal selected from the group consisting of molybdenum (Mo), chromium (Cr), tungsten (W), manganese (Mn), nickel (Ni), iron (Fe), zinc (Zn), cobalt (Co), copper (Cu), tin (Sn), vanadium (V) and mixtures thereof, optionally promoted by an alkali metal sulfide. In the broad practice of the invention, the porous alumina support may be alumina, silica-alumina, calcium aluminate, kieselguhr, and various clays or refractory materials. Alumina or activated alumina is a preferred support material. The porous alumina support particles may have a diameter of from about 0.4 to about 0.7 micron and preferably will have a specific surface area of at least about 1 $m^2/g$, more usually at least about 5 $m^2/g$, preferably at least about 40 $m^2/g$ and sometimes at least about 100 $m^2/g$. Commercially available aluminas suitable for practicing the present invention have specific surface areas in the range of 100 to 300 $m^2/g$. These catalyst compositions are known in the prior art and their preparation is described, for example, in Buchholz, U.S. Pat. No. 4,410,731; Haines, U.S. Pat. No. 4,449,006 and 4,536,492; Barrault et al., *Applied Catalysis*, 33:309–330 (1987) and Boulinguiez et al., U.S. Pat. No. 4,665,242, the disclosures of which are incorporated herein by reference.

Briefly, a metal oxide(s) of a metal selected from molybdenum (Mo), chromium (Cr), tungsten (W), manganese (Mn), nickel (Ni), iron (Fe), zinc (Zn), cobalt (Co), copper (Cu), tin (Sn), vanadium (V) and mixtures thereof first is introduced onto a porous alumina support. This can be accomplished by impregnation techniques well-known in the art, such as incipient wetness. The metal oxide impregnated alumina then is sulfided by contacting (pretreating) the catalyst with substantially pure hydrogen sulfide (or a mixture of hydrogen and sulfur) at an elevated temperature or by subjecting the metal oxide impregnated alumina to the reaction conditions during start-up. Again, conditions for sulfactivating the catalyst are described in the abovementioned patents.

In a preferred embodiment, the catalyst also includes a promoter of an alkali metal which is co-impregnated on the catalyst prior to the sulfactivation process. The promoter can be easily provided by impregnating the alumina with a solution of the metal oxide and an alkali metal hydroxide or salt. Often an alumina support bearing an impregnated metal oxide can be obtained from a commercial source and is then further impregnated with the alkali metal promoter. Again, such promoted metal oxide catalysts are known, for example, from Buchholz, U.S. Pat. No. 4,410,731; Haines, U.S. Pat. Nos. 4,449,006 and 4,536,492; Barrault et al., *Applied Catalysis*, 33:309–330 (1987) and Boulinguiez et al., U.S. Pat. No. 4,665,242. Preferred alkali metals include potassium, rubidium and cesium.

The catalyst comprises from about 10 to 90 weight percent of the alumina support and conversely 90 to 10 weight percent of the optionally promoted metal oxide, on the basis of the combined supported metal oxide-alumina catalyst. Preferably, the metal oxide comprises from 65 to 95 percent by weight of the combination of metal oxide and alkali metal promoter.

The metal oxide of the supported metal oxide catalyst used in the second catalytic reaction is accommodated in the support primarily as a two-dimensional metal oxide overlayer, with the oxide having a non-crystalline form. Supported metal oxide catalysts useful in the second process step of this invention generally comprise a metal oxide substrate, such as titania, silica, zirconia, alumina, niobia, ceria, magnesia, lanthanum oxide, tin oxide and mixtures thereof, whose surface has been modified with a layer of an oxide of a metal or a mixture of metal oxides as identified above (e.g., preferably an oxide of vanadium, and oxide mixtures containing vanadium) in an amount such that the catalyst exhibits properties different from the metal oxide substrate whose surface has not been modified. The support and the supported metal should not be the same. These catalysts also behave differently from bulk metal oxides made from the metal oxide overlayer component (e.g., bulk oxides of vanadium, and its mixtures). Consequently, in this embodiment of the invention, the metal oxide loading on the metal oxide support or substrate, e.g., titania, must be sufficient to modify the metal oxide surface, but not enough to result in a catalyst exhibiting properties of a bulk oxide made from the metal oxide overlayer component, e.g., a bulk oxide of vanadia. Thus, at least a portion of and preferably at least about 25 wt % of the metal oxide coating will be in a non-crystalline form. Additionally, the metal oxide loading on the metal oxide support or substrate broadly ranges between about 0.5 to 35 wt % of the total catalyst weight.

A preferred metal oxide support for use in the second step of the process is titania (titanium dioxide) which can be employed in the anatase or rutile form. For example at least about 25 wt % (and generally from about 50 to about 100 wt %) of the titanium dioxide ($TiO_2$) can be in the anatase form. As recognized by those skilled in the catalytic art, the titania support material needs to be judiciously evaluated since certain grades may have impurities that interfere with the catalytic activity. Normally, with recognition of the previous caveat, the titanium dioxide may be prepared by any conventional technique. The titanium dioxide used in the catalyst of this invention may be composed of substantially porous particles of a diameter of from about 0.4 to about 0.7 micron and preferably has a specific surface area of at least about 1 $m^2/g$, more usually at least about 5 $m^2/g$, preferably at least about 40 $m^2/mg$ and sometimes at least about 100 $m^2/g$.

The metal oxide supported catalysts used in the second step of the process of this invention may be prepared by impregnation techniques well-known in the art, such as incipient wetness, grafting, equilibrium adsorption, vapor deposition, thermal spreading, etc. When using an incipient wetness impregnation technique, an aqueous or non-aqueous solution containing a metal oxide precursor compound is contacted with the metal oxide support or substrate material, e.g., titania, for a time sufficient to deposit a metal oxide precursor material onto the support such as by selective adsorption or alternatively, excess solvent may be evaporated leaving behind the precursor compound or salt. If an incipient wetness impregnation technique is used to prepare a catalyst of this invention, the metal oxide precursor (e.g., salt) solution used may be aqueous or organic, the only requirement being that an adequate amount of a precursor compound for the selected metal oxide be soluble in the solvent used in preparing this solution. Other impregnation techniques, such as vapor deposition and thermal spreading, do not require use of a solvent as does incipient wetness, and may be desirable in some circumstances to avoid the problem of volatile organic carbon (VOC) emissions.

For example, one way to disperse vanadium oxide, tungsten oxide or a combination of the two oxides onto a titania metal oxide support or substrate is to impregnate titania spheres or powder (spheres or powder are used as representative examples of shapes of titania) with a solution containing a vanadium or a tungsten compound. When impregnating a substrate with both oxides, the tungsten and vanadium are introduced in a stepwise manner, tungsten first, followed by vanadium, with appropriate intermediate drying and calcining steps. Each solution may be an aqueous solution, one using an organic solvent or a mixture of the two. Generally, an aqueous solution is preferred. Criteria used to choose the vanadium and tungsten compounds include whether the compounds are soluble in the desired solvent and whether the compounds decompose at an acceptable rate at a high, calcination temperature to give the appropriate metal oxide. Illustrative of suitable compounds of vanadium and tungsten are the halides of vanadium and tungsten, oxyacids, oxyacid salts and oxysalts of vanadium and tungsten. Specific examples are tungsten dibromide, tungsten pentabromide, tungsten tetrachloride, tungsten dioxydichloride, tungstic acid, ammonium meta-tungstate, vanadium tribromide, vanadium dichloride, vanadium trichloride, vanadium oxychloride, vanadium oxydichloride, vanadic acid, vanadyl sulfate, vanadium alkoxides, vanadium oxalate (which may be formed in situ by reaction of $V_2O_5$ and an aqueous solution of oxalic acid), and ammonium meta-vanadate. Suitable metal oxide precursor compounds for the other metal species suitable for making the supported metal oxide catalysts of this invention are well recognized by those skilled in the catalysis art.

The impregnation of the metal oxide support or substrate, e.g., titania support spheres or powdered, with the metal oxide precursor compound solution may be carried out, as noted above, in ways well known in the art using either wet or dry impregnation techniques. One convenient method is to place the metal oxide support or substrate, e.g., titania particles, into a rotary evaporator which is equipped with a steam jacket. An impregnating solution of a precursor compound which contains an amount of the desired metal to be included in the finished catalyst (as the metal) is added to the support particles and the mixture is cold rolled (no steam) for a time from about 10 to 60 minutes sufficient to impregnate the support with the precursor compound solution. Next, steam is introduced and the solvent is evaporated from the impregnated solution. This usually takes from about 1 to about 4 hours. The impregnated support will normally be dried at temperatures ranging from about 50°–300° C. to remove excess solvent.

Water soluble precursor compounds are generally preferred for industrial applications because of the environmental concern about VOC emissions. Nonetheless, when using an organic solvent, initial heating may be done in a nitrogen atmosphere to remove any flammable solvent. Finally, the support particles are removed from the rotary evaporator and calcined in a suitable oxidizing atmosphere such as air, oxygen, etc. at a temperature of about 150° to 800° C., and more usually from 400°–600° C., preferably for about 1 to about 3 hours, sufficient to decompose the precursor compound to the corresponding metal oxide. In other cases, as recognized by those skilled in the art, calcining conditions need to be adjusted to avoid undesirably reducing surface area.

Because some precursor compounds are air/moisture sensitive, they are prepared under a nitrogen atmosphere as is recognized by those skilled in this art. The time required to calcine the composite will, of course, depend on the temperature and in general will range from about 0.5–7 hours. Calcination at 450° C. for about 2 hours has proven to be suitable for 1% vanadia on titania catalyst. The precise time and temperature for calcination depends on the particular metal oxide overlayer and should be selected to avoid adversely affecting the metal oxide support, e.g., in the case of a titania metal oxide support, to avoid substantial crystal phase transformation of the anatase into another crystalline form, e.g., rutile, and degradation of extended surface area.

Reducing atmospheres may also be used to decompose the transition metal oxide precursors. To avoid potential safety concerns, the resulting composite should be calcined to convert the reduced metal component to the oxide form. If the support is to be provided with an overlayer of a combination of metal oxides, e.g., if an overlayer containing both vanadium and tungsten oxide is desired, then the metal oxide precursor compounds may be impregnated on the metal oxide support simultaneously, but preferably are impregnated sequentially as previously noted.

The metal oxide supported catalysts used in the process of this invention will generally have surface metal oxide loadings of from about 0.5 to 35 wt. % metal oxide based on the total active catalyst composition, preferably from about 1 to 20 wt. %, more usually from about 1–15 wt. %, and most preferably 1–10 wt. % based on the total active catalyst composition.

While titania, silica, zirconia, alumina, niobia, ceria, magnesia, lanthanum oxide and tin oxide are conveniently referred to as supports or substrates in the description of the preferred embodiment of the present invention, based to a large degree on the way the catalyst is prepared, it should be noted that they provide important roles as active catalytic components in the supported metal oxide catalyst. Combination supports may also be advantageous for use in catalysts suitable for practicing the second step of the process of this invention. For example, substrates constituting a mixture of titania and zirconia or titania and silica can be used.

Further details on the preparation and structure of such metal oxide supported catalysts useful in the practice of the present invention can be found in Jehng et al., *Applied Catalysis A*, 83, (1992) 179–200; Kim and Wachs, *Journal of Catalysis*, 142, 166–171; Jehng and Wachs, *Catalysis Today*, 16, (1993) 417–426; Kim and Wachs, *Journal of Catalysis*, 141, (1993) 419–429; Deo et al., *Applied Catalysis A*, 91, (1992) 27–42; Deo and Wachs, *Journal of Catalysis*, 146, (1994) 323–334; Deo and Wachs, *Journal of*

Catalysis, 146, (1994) 335–345; Jehng et al., *J. Chem. Soc. Faraday Trans.*, 91(5), (1995) 953–961; Kim et al., *Journal of Catalysis*, 146, (1994) 268–277; Banares et al., *Journal of Catalysis*, 150, (1994) 407–420 and Jehng and Wachs, *Catalyst Letters*, 13, (1992) 9–20, the disclosure of which are incorporated herein by reference.

Preferred supported metal oxide catalysts for the second step of the process are those which are known to be suitable for converting methanol to formaldehyde. Particularly preferred are supported metal oxide catalysts comprising a vanadia overlayer on a titania support.

It often is desired that the metal oxide, such as titania, silica, zirconia, alumina, niobia, magnesia, ceria, lanthanum oxide, tin oxide, and their mixtures, used as a catalyst support component in accordance with the present invention have a surface area in the range of about 1 to about 150 m$^2$/g and higher. These materials may be used in any configuration, shape or size which exposes their surface and any metal oxide layer dispersed thereon to the gaseous stream passed in contact therewith. For example, these oxide supports, such as titania can conveniently be employed in a particulate form or deposited (before or after impregnation with the metal oxide overlayer) on a monolithic carrier or onto ceramic rings or pellets. As particles, the support, such as titania, can be formed in the shape of pills, pellets, granules, rings, spheres and the like. Use of free particulates might be desirable when large catalyst volumes are needed or if the catalyst bed is operated in a fluidized state. A monolithic form or deposition of the active catalyst on an inert ceramic support might be preferred in applications where catalyst movement is to be avoided because of concerns about catalyst attrition and dusting, and a possible increase in pressure drop across a particulate bed. In a preferred approach, a metal oxide supported catalyst, such as a vanadia on titania catalyst, may be deposited on a ceramic carrier such as silicon carbide, silicon nitride, carborundum steatite, alumina and the like, provided in the shape of rings or pellets. Typically, the active catalyst will be applied to the inert ceramic support in an amount to provide 1 to 15% by weight of the supported catalyst.

As noted, the present invention also contemplates the use of bulk metal oxides as the catalyst for converting methyl mercaptan to formaldehyde. Such bulk metal oxide catalysts generally constitute molybdates (Mo), chromates (Cr), vanadates (V), rhenates (Re), titanates (Ti), niobates (Nb), tungstates (W) and mixtures thereof Such metal oxides also contain a wide variety of other metal species such as alkali metals (e.g., sodium (Na), lithium (Li), potassium (K) and cesium (Cs)), alklaine earth metals (e.g., calcium (Ca), barium (Ba), and magnesium (Mg)) and transition metals (e.g., copper (Cu), nickel (Ni), cobalt (Co), aluminum (Al), lead (Pb), bismuth (Bi), iron (Fe), zinc (Zn), cadmium (Cd), tellurium (Te), manganese(Mn)). Those skilled in the art recognize the wide variety of available bulk metal oxide catalysts. As a general rule, those bulk metal oxide catalysts known to be suitable for converting methanol to formaldehyde also may be suitable for the methyl mercaptan to formaldehyde conversion of the present invention.

Methods for making bulk metal oxide catalysts used in the present invention also are well known to those skilled in the art. In particular, the active catalyst can be prepared by physically blending the metal oxides, by coprecipitation from aqueous solutions containing soluble compounds of the catalyst components in the desired molar ratio or by any other technique which provides an intimate mixture of the metal oxide constituents. For example, an aqueous solution of a water-soluble molybdenum compound (ammonium heptamolybdate) is mixed with a water-soluble iron compound (ferric chloride) to cause coprecipitation of both molybdenum and iron, using procedures well known to those skilled in the art. The coprecipitate is washed, to eliminate the soluble salts formed during the coprecipitation reactions, filtered, dried and calcined to convert the metal constituents to their active iron molybdate (oxide) form. Those skilled in the art recognize a variety of water soluble metal compounds that can be used to prepare the active catalyst. Alternatively, oxides of the respective metals may be ground together and calcined. Additional details on bulk metal oxides and bulk metal oxide catalysis can be found in Arora et al., *Journals of Catalysis*, 159, (1996) 1–13, which is incorporated herein by reference.

Those skilled in the art recognize that there exists a wide range of compounds, generally used in admixture, suitable for preparing bulk metal oxide catalysts. The following is a representative, though not exhaustive, list of possible constituents: bulk vanadates such as $PbV_2O_6$, $NaVO_3$, $Na_3VO_4$, $BiVO_4$ and other Bi—V—O family members, $AlVO_4$, $FeVO_4$, $Mg_3(VO_4)_2$, $Mg_2V_2O_7$, $CeVO_4$, $Zn_3(VO_4)_2$, $CdV_2V_2O_7$, $Zn_2V_2O_7$, $VOPO_4$ and other V—P—O family members, $KVO_3$, $Pb_2V_2O_7$, and $TlVO_4$; bulk molybdates such as $PbMoO_4$, $CaMoO_4$, $Bi_2Mo_2O_9$, $Bi_3(FeO_4)(MoO_4)_3$ and other Bi—Mo—O family members, $Na_2MoO_4$, $MnMoO_4$, $Gd_2(MoO_4)_3$, $MgMoO_4$, $CuMoO_4$, $CoMoO_4$, $Fe_2(MoO_4)_3$, $Te_2MoO_7$, $NiMoO_4$, $Al_2(MoO_4)_3$, $Cr_2(MoO_4)_3$, and $Na_2Mo_2O_7$; bulk niobates such as $YNbO_4$, $YbNbO_4$, $LiNbO_3$, $NaNbO_3$, $KNbO_3$, $AlNbO_4$, $K_8Nb_6O_{19}$, $BiNbO_4$, and other Bi—Nb—O family members, $SbNbO_4$, $NbOPO_4$, $CaNb_2O_6$, $K_4Nb_6O_{17}$, and $KCa_2Nb_3O_{10}$; bulk tungstates such as $Li_6WO_6$, $FeWO_4$, $CoWO_4$, $MnWO_4$, $NiWO_4$, $CuWO_4$, $CaWO_4$, $Cs_2WO_4$, $Na_2WO_4$, $B_aWO_4$, $Fe_2(WO_4)_3$, $Al_2(WO_4)_3$, $Al_2(WO_4)_3$, $SrWO_4$, $K_2WO_4$, $Na_2W_2O_7$, $Li_2WO_4$, $CsLuW_2O_8$, $BiWO_4$, and other Bi—W—O family members; bulk chromates such as $Na_2CrO_4$, $Na_2Cr_2O_7$, $Na_2Cr_3O_{10}$, $Na_2Cr_4O_{13}$, $K_2CrO_4$, $K_2Cr_2O_7$, $K_2Cr_3O_{10}$, $K_2Cr_4O_{13}$, $Fe_2(CrO_4)_3$, $CaCrO_4$, $Cs_2CrO_4$, $BiCrO_4$ and other Bi—Cr—O family members; bulk rhenates such as $NaReO_4$, $Li_6ReO_4$, and $Mg(ReO_4)_2$; bulk titanates such as $Na_2TiO_4$, $NaTiO_3$, $BaTiO_4$, $BaTiO_3$, and other Ba—Ti—O family members and bulk manganates such as $MnAl_2O_4$, $KMnO_4$, $MnO$, $MnO_2$, $Mn_2O_3$, and $Mn_3O_4$.

To achieve high selectivity in the conversion of methyl mercaptan to formaldehyde it is important to maintain the flow rate of methyl mercaptan per unit mass of catalyst in the range of $10^{-2}$ to $10^4$ cubic centimeters (STP) of methyl mercaptan per gram of active catalyst per minute (excluding inert ceramic components or other inert support material). Generally, higher reaction temperatures permit higher flow rates. Usually, the process can be operated at $10^{-1}$ to $10^2$, cubic centimeters (STP) of methyl mercaptan per gram of catalyst per minute.

As used herein, the term "selectively" is intended to embrace the conversion of at least 1% of the methyl mercaptan, preferably at least 10% of the methyl mercaptan, more usually at least 50% of the methyl mercaptan and most preferably at least 70% of the methyl mercaptan which contacts the catalyst to formaldehyde. Selectivity, as that term is used herein, is determined by the percentage of formaldehyde in the mercaptan conversion products as a proportion of the carbon-containing mercaptan oxidation products.

The oxidation reaction of the second step is exothermic. As recognized by those skilled in the art a variety of reactor designs may be employed to accommodate the necessary mass and heat transfer processes for effective operation on a continuous basis. The reaction may be conducted at atmosphere pressure, and above or below atmospheric pressure.

EXAMPLES

To facilitate a more complete understanding of the invention, a number of Examples are provided below. The scope of the invention, however, is not limited to specific embodiments disclosed in these Examples, which are for purposes of illustration only.

Catalyst Preparation and Characterization

Supported metal oxide catalysts were prepared as follows

Preparation Example 1

Vanadia on Titania

A vanadia on titania metal oxide supported catalyst was prepared in accordance with the following procedure. The vanadia-titania catalyst was prepared by using $TiO_2$ (Degussa P25) as the support. The $TiO_2$ support (~10% rutile and ~90% anatase) possessed a surface area of ~55 $m^2/g$. It was calcined in air at 500° C. and cooled to room temperature before impregnation with the vanadium oxide precursor. The vanadium oxide overlayers on the $TiO_2$ support were prepared from vanadium triisopropoxide oxide (Alfa, 95–98% purity) by the incipient wetness impregnation method. The preparation was performed under a nitrogen environment and in nonaqueous solutions, since the alkoxide precursor is air and moisture sensitive. Solutions of known amounts of vanadium triisopropoxide oxide and propanol-2, corresponding to the incipient wetness impregnation volume and the final amount of vanadium required, were prepared in a glove box filled with nitrogen. The solutions of the vanadium precursor and propanol-2 were then thoroughly mixed with the titania support and dried at room temperature in the glove box for 24 hr. The impregnated samples were heated to 300° C. in flowing nitrogen and the final calcination was performed in $O_2$ (Linde, 99.9% pure) at 500° C. for 15 hours. The catalyst was then pelletized, crushed and sieved to obtain catalyst particles sizes between 100 to 200 $\mu m$.

Preparation Example 1A

Vanadia on Titania

Another vanadia on titania metal oxide supported catalyst was prepared using the general procedure of Preparation Example 1 except that the final calcination was conducted at 450° C. for 2 hours.

Preparation Example 2

Molybdenum Oxide on Titania

An aqueous solution of ammonium heptamolybdate (($NH_4$)$_6$$Mo_7O_{24}$·$4H_2O$) (Alfa) was deposited onto $TiO_2$ (Degussa P25) as the support (~10% rutile and ~90% anatase) by the incipient wetness technique. As in Example 1, the support was calcined in air at 500° C. and cooled to room temperature before impregnation with the molybdenum oxide precursor. The support possessed a surface area of ~55 $m^2/g$. After impregnation, the wet samples were dried at room temperature for 16 hours, further dried at 110–120° C. for 16 hours and calcined at 450° C. for 12 hours. The catalyst was then pelletized, crushed and sieved to obtain catalyst particles sizes between 100 to 200 $\mu m$.

Preparation Example 3

Chromia on Titania

An aqueous solution of chromium nitrate (Cr($NO_3$)$_3$·$9H_2O$) (Allied Chemical Co.) was deposited onto $TiO_2$ (Degussa P25) as the support using the incipient wetness technique. As in the previous Examples, the $TiO_2$ support (~10% rutile and ~90% anatase) was calcined in air at 500° C. and cooled to room temperature before impregnation with the chromium precursor. The support possessed a surface area of ~55 $m^2/g$. After impregnation, the wet samples were dried at room temperature for 16 hours, further dried at 110–120° C. for 16 hours and calcined at 450° C. for 13 hours. The catalyst was then pelletized, crushed and sieved to obtain catalyst particles sizes between 100 to 200 $\mu m$.

Preparation Example 4

Rhenium Oxide on Titania

An aqueous solution of perrhenic acid ($HReO_4$) (Aldrich) was deposited onto $TiO_2$ (Degussa P25) as the support using the incipient wetness technique. As before, the $TiO_2$ support (~10% rutile and ~90% anatase) was calcined in air at 500° C. and cooled to room temperature before impregnation with the rhenium oxide precursor. The support possessed a surface area of ~55 $m^2/g$. After impregnation, the wet samples were dried at room temperature for 16 hours, further dried at 110–120° C. for 16 hours and calcined at 450° C. for 13 hours. The catalyst was then pelletized, crushed and sieved to obtain catalyst particles sizes between 100 to 200 $\mu m$.

Preparation Example 5

Vanadia on Zirconia

A vanadium oxide overlayer was deposited onto a zirconium oxide ($ZrO_2$) support (Degussa) having a surface area ~39 $m^2g^{-1}$ using an organic solution of vanadium triisopropoxide oxide (Alfa, 95–98% purity). In particular, the vanadium overlayer was prepared by the incipient wetness impregnation method using a solution of vanadium triisopropoxide oxide and propanol-2 in a glove box filled with nitrogen. The solutions of the vanadium precursor and propanol-2 were thoroughly mixed with the zirconia support and dried at room temperature for 16 hours, further dried at 110–120° C. for 16 hours and calcined at 450° C. for 16 hours. The catalyst was then pelletized, crushed and sieved to obtain catalyst particles sizes between 100 to 200 $\mu m$.

Preparation Example 6

Vanadia on Niobia

A vanadium oxide overlayer was deposited on a niobia ($Nb_2O_5$) support (55 $m^2g^{-1}$) using vanadium triisopropoxide oxide (Alfa, 95–98% purity) and the incipient wetness technique. The niobia support was prepared by calcining niobic acid (Niobia Products Co.) at 500° C. for two hours. A solution of vanadium triisopropoxide oxide and propanol-2 was thoroughly mixed with the niobia support in a glove box filled with nitrogen, dried at room temperature for 16 hours, further dried at 110–120° C. for 16 hours and calcined at 450° C. for 16 hours. The catalyst was then pelletized, crushed and sieved to obtain catalyst particles sizes between 100 to 200 $\mu m$.

Preparation Example 7

Vanadia on Alumina

A vanadium oxide overlayer was deposited on an alumina ($Al_2O_3$) support (Harshaw, 180 $m^2g^{-1}$) using an organic solution of vanadium triisopropoxide oxide (Alfa, 95–98% purity) and the incipient wetness impregnation. A solution of the vanadium precursor and propanol-2 was thoroughly mixed with the alumina support, in a glove box filled with nitrogen, dried at room temperature for 16 hours, further dried at 110–120° C. for 16 hours and calcined at 500° C. for 16 hours. The catalyst was then pelletized, crushed and sieved to obtain catalyst particles sizes between 100 to 200 µm.

Preparation Example 8

Vanadia on Silica

A vanadium oxide overlayer was deposited on an silica ($SiO_2$) support (Cab—O—Sil, 300 $m^2g^{-1}$) using an organic solution of vanadium triisopropoxide oxide (Alfa, 95–98% purity) and the incipient wetness impregnation. A solution of the vanadium precursor and propanol-2 was thoroughly mixed in a glove box filled with nitrogen with the $SiO_2$ support, the wet silica was dried at room temperature for 16 hours, further dried at 110–120° C. for 16 hours and calcined at 500° C. for 16 hours. The catalyst was then pelletized, crushed and sieved to obtain catalyst particles sizes between 100 to 200 µm.

Preparation Example 9

Tungsten Oxide on Silica

An aqueous solution of ammonium metatungstate (($NH_4)_6H_2W_{12}O_{40}\cdot xH_2O$) (Pfaltz & Bauer, 99.9% purity) was deposited as an oxide overlayer onto a silica ($SiO_2$) support (Cab—O—Sil, 300 $m^2g^{-1}$) using the incipient wetness technique. After impregnation, the silica support was dried at room temperature for 16 hours, further dried at 110–120° C. for 16 hours and calcined at 500° C. for 16 hours. The catalyst was then pelletized, crushed and sieved to obtain catalyst particles sizes between 100 to 200 µm.

Preparation Example 10

Niobia on Silica

An aqueous solution of niobium oxalate (Niobium Products Co.) was deposited onto a silica ($SiO_2$) support (Cab—O—Sil, 300 $m^2g^{-1}$) using the incipient wetness technique. After impregnation, the silica support was dried at room temperature for 16 hours, further dried at 110–120° C. for 16 hours and calcined at 500° C. for 16 hours. The catalyst was then pelletized, crushed and sieved to obtain catalyst particles sizes between 100 to 200 µm.

Preparation Example 11

Titania on Silica

Titanium isopropoxide (Aldrich) in a toluene solution was impregnated onto a silica ($SiO_2$) support (Cab—O—Sil, 300 $m^2g^{-1}$) under a nitrogen blanket to form a titania overlayer using the incipient wetness technique. After impregnation, the wet silica was dried at room temperature for 16 hours, further dried at 110–120° C. for 16 hours and calcined at 500° C. for 16 hours. The catalyst was then pelletized, crushed and sieved to obtain catalyst particles sizes between 100 to 200 µm.

Preparation Example 12

Vanadia and Tungsten Oxide on Titania

A vanadia and tungsten oxide on titania catalyst was prepared by a two step incipient wetness impregnation method. A vanadium oxide overlayer was deposited first on the $TiO_2$ support using a solution of vanadium triisopropoxide oxide (Alfa, 95–98% purity) and propanol-2 by the incipient wetness impregnation method in a glove box filled with nitrogen. The solution of the vanadium precursor and propanol-2 were thoroughly mixed with the $TiO_2$ (Degussa P25) as the support. The $TiO_2$ support (~10% rutile and ~90% anatase) was prepared by previous calcination in air at 500° C. and cooled to room temperature before impregnation with the vanadium oxide precursor. The support possessed a surface area of ~55 $m^2/g$. After impregnation, the wet $TiO_2$ was dried at room temperature for 16 hours, further dried at 110–120° C. for 16 hours and calcined at 450° C. for 12 hours. Subsequently, an aqueous solution of ammonium metatungstate (($NH_4)_6H_2W_{12}O_{40}\cdot xH_2O$) was deposited as an oxide overlayer onto the $TiO_2$ support, again using the incipient wetness technique. After impregnation, the wet samples were dried at room temperature for 16 hours, further dried at 110–120° C. for 16 hours and calcined at 500° C. for 16 hours. The catalyst was then pelletized, crushed and sieved to obtain catalyst particles sizes between 100 to 200 µm.

Preparation Example 13

Vanadia and Titania Silica

A vanadia and titania on silica catalyst was prepared by a two step incipient wetness impregnation method. The silica support used for this study was Cabosil EH-5 (380 $m^2/g$). This fluffy material was treated with water in order to condense its volume for easier handling. Then the wet $SiO_2$ was dried at 120° C. and subsequently calcined at 500° C. overnight. The resulting surface area was 332 $m^2/g$. This water pretreatment did not change the dispersion ability of the silica, since an isopropanol pretreated silica also resulted in the same surface area and the same dispersion capacity. A titanium oxide overlayer was deposited first on the silica ($SiO_2$) support under a nitrogen blanket using titanium isopropoxide (Aldrich) in a toluene solution by the incipient wetness impregnation method in a glove box filled with nitrogen. After impregnation, the loaded sample was dried at room temperature for 16 hours, further dried at 110–120° C. for 16 hours and calcined at 500° C. for 4 hours. Subsequently, a solution of vanadium triisopropoxide oxide (Alfa, 95–98% purity) and propanol-2 was impregnated onto the silica ($SiO_2$) support containing titania again using the incipient wetness technique. The solution of the vanadium precursor and propanol-2 was thoroughly mixed with the $SiO_2$ support containing titania. After impregnation, the wet $SiO_2$ was dried at room temperature for 16 hours, further dried at 110–120° C. for 16 hours and calcined at 450° C. for 2 hours. The catalyst was then pelletized, crushed and sieved to obtain catalyst particles sizes between 100 to 200 µm.

The above-synthesized catalysts, as well as one other bulk metal oxide catalyst, were examined for their ability to oxidize methyl mercaptans selectively to formaldehyde generally using the following equipment and methods.

Catalytic Reactor

The oxidation reactions were carried out in an isothermal fixed-bed integral mode reactor operating at atmospheric pressure. The methanethiol ($CH_3SH$) diluted in helium, was supplied by Scott Specialty Gases. The reactant gas was further diluted in helium and air (Blue Valley Welding Supply, total hydrocarbons concentration <1 ppm, $H_2O$ concentration <3 ppm) and sent to the reactor through glass tubing connected with Teflon fittings. Flow rates and concentrations were controlled by two mass flow controllers (Brooks 5850 D, 1–100 sccm for helium and Omega FMA-767-V, 0–1 slpm). The lines were heated to 70° C. for the methanethiol oxidation studies to prevent condensation. The total gas flow was maintained between 150 and 200 ml/min. The reactor was kept in a vertical position and made of 6-mm O.D. Pyrex glass. Heating tape was used in conjunction with a feedback temperature controller (Omega CN 9000) to obtain the desired reactor temperature. The catalysts were held at the middle of the reactor tube between a porous glass frit, pore size of 40 to 60 μm, and a glass wool plug. Each catalyst sample was always pretreated by heating at 500° C. for 2 to 3 hours in flowing air, to remove adsorbed water on the catalyst surface prior to initiation of an experiment. The outlet of the reactor was connected to an FTIR cell (Infrared Analysis, Inc; Model #G-4-Tin—Ta—Ba—Ag), which was used to analyze the reaction products. The lines between the outlet and the cell were heated to avoid condensation of the products. The flow of reaction products sent to the FTIR cell was controlled by a needle valve (Nupro Company, SS-4BRG).

Composition Analysis by FTIR

Analysis of the reaction products was accomplished using a Midac Inc. FTIR, (model #101250, series 2–4). Samples were analyzed in a path gas cell (Infrared Analysis, Inc; Model # G-4-Tin-Ta-Ba-Ag), which has an effective length of 10 m and a volume of 3.1 L. The spectrometer was controlled by a microcomputer (Sprouse Scientific, model TECH-1000 A) to provide acquisition and manipulation of the spectra: display, subtraction, zoom, etc. The spectra were obtained using 16 scans at a resolution of 0.5 $cm^{-1}$. The FTIR analysis required about 10 minutes.

Methanethiol oxidation was investigated with a variety of supported metal oxide and bulk metal oxide catalysts as follows:

Example 1

In a series of experiments, a supported oxide catalyst prepared in accordance with Preparation Example 1, comprising about 1% vanadia ($V_2O_5$) on titania ($TiO_2$) catalyst, was contacted with a nitrogen stream containing methanethiol over a wide temperature range in order to optimize the formation of formaldehyde. Mercaptan conversions were measured by both increasing and decreasing the temperature between 200 and 450° C., and no temperature hysteresis was observed. The reaction products of this methanethiol oxidation over the 1% $V_2O_5/TiO_2$ catalyst as a function of temperature is graphically presented in FIG. 1. As illustrated, formaldehyde was found to be the predominant product. In these tests, dimethylthiomethane ($H_2C(SCH_3)_2$) was observed as an intermediate between 200 to 300° C., and dimethyl disulfide ($CH_3S)_2$ was found as an intermediate between 300 to 400° K. Carbon monoxide and carbon dioxide appeared in small amounts as reaction products; but the formation of CO increased at elevated temperatures. Sulfur dioxide production tracked the formation of formaldehyde.

Examples 2–16

Using substantially the same equipment and procedures as Example 1, a variety of both metal oxide supported catalysts and a bulk metal oxide catalyst were tested for their ability to oxidize methanethiol selectively to formaldehyde. While the majority of the data were obtained at a reaction temperature of 350° C., Examples 8, and 12–14 were run at 400° C., since formaldehyde was not detected in the product using these catalysts at 350° C. The feed gas contained 1150 ppm of methanethiol and was introduced into the reactor at a volumetric flow rate of 150 ml/min. The iron-molybdate catalyst contained iron ($Fe_2O_3$) and molybdenum ($MoO_3$) in a molar ratio (Fe:Mo) of 1.0/2.15 and was obtained from Perstorp. The results of these tests are reported in Table 1.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

TABLE 1

| Example | Catalyst | Preparation Example | Catalyst Load (mg) | Conversion of $CH_3SH$ (Mole %) | Selectivity (mol%) | | | |
|---|---|---|---|---|---|---|---|---|
| | | | | | Formaldehyde | Carbon Monoxide | Carbon Dioxide | COS |
| 2 | 1.15% $V_2O_5/TiO_2$ | 1 | 10 | 54 | 78% | 11% | 3% | 8% |
| 3 | 1% $V_2O_5/TiO_2$ | 1A | 10 | 48 | 84 | 10 | 4 | 2 |
| 4 | 1% $MoO_3/TiO_2$ | 2 | 100 | 84 | 79 | 12 | 9 | 0 |
| 5 | 1% $CrO_3/TiO_2$ | 3 | 100 | 79 | 81 | 12 | 7 | 0 |
| 6 | 1% $Re_2O_7/TiO_2$ | 4 | 10 | 80 | 76 | 18 | 3 | 2 |
| 7 | $Fe_2(MoO_4)_3$ + $MoO_3$ | — | 100 | 40 | 85 | 10 | 5 | 0 |
| 8 | 1% $V_2O_5/ZrO_2$ | 5 | 10 | 57 | 89 | 8 | 2.6 | .4 |
| 9 | 1% $V_2O_5Nb_2O_5$ | 6 | 20 | 45 | 72 | 21 | 7 | 0 |
| 10 | 1% $V_2O_5/Al_2O_3$ | 7 | 100 | 61 | 37 | 16 | 6 | 41 |
| 11 | 1% $V_2O_5/SiO_2$ | 8 | 100 | 63 | 84 | 9 | 7 | 0 |
| 12 | 1% $WO_3/SiO_2$ | 9 | 100 | 46 | 49 | 11 | 4 | 36 |
| 13 | 2.5% $Nb_2O_5/SiO_2$ | 10 | 100 | 42 | 50 | 13 | 2 | 35 |
| 14 | 10% $TiO_2/SiO_2$ | 11 | 100 | 45 | 65 | 16 | 3 | 16 |
| 15 | 1% $V_2O_5/7\% WO_3/TiO_2$ | 12 | 10 | 52 | 82 | 14 | 4 | 0 |
| 16 | 10% $V_2O_5/$ 15% $TiO_2/SiO_2$ | 13 | 100 | 71 | 85 | 8 | 7 | 0 |

What is claimed is:

1. A process for producing formaldehyde from a gas stream containing hydrogen, a carbon oxide and hydrogen sulfide ($H_2S$) comprising contacting the gas stream with a first catalyst comprising a porous alumina supported sulfided metal oxide of a metal selected from the group consisting of molybdenum (Mo), chromium (Cr), tungsten (W), manganese (Mn), nickel (Ni), iron (Fe), zinc (Zn), cobalt (Co), copper (Cu), tin (Sn), vanadium (V) and mixtures thereof, optionally promoted by an alkali metal sulfide, to convert said hydrogen, carbon oxide and hydrogen sulfide ($H_2S$) to methyl mercaptan and then contacting the methyl mercaptan with a second catalyst selected from a supported metal oxide catalyst and a bulk metal oxide catalyst under oxidizing conditions for a time sufficient to convert at least a portion of the methyl mercaptan to formaldehyde and sulfur dioxide, and recovering said formaldehyde.

2. The process of claim 1 wherein the supported metal oxide second catalyst has a metal oxide overlayer of a metal selected from the group consisting of titanium (Ti), zirconium (Zr), molybdenum (Mo), rhenium (Re), vanadium (V), chromium (Cr), tungsten (W), manganese (Mn), niobium (Nb), tantalum (Ta) and mixtures thereof.

3. The process of claim 2 wherein the supported metal oxide second catalyst has a metal oxide support selected from the group consisting of titania, silica, zirconia, alumina, niobia, magnesia, ceria, lanthanum oxide, tin oxide and mixtures thereof with the proviso that the metal of the metal oxide overlay and the metal oxide support are not the same.

4. The process of claim 3 wherein the supported metal oxide second catalyst is selected from the group consisting of a vanadia overlayer on a titania support, a molybdenum oxide overlayer on a titania support, a chromium oxide overlayer on a titania support, a rhenium oxide overlayer on a titania support, a vanadia overlayer on a zirconia support, a vanadia overlayer on a niobia support, a vanadia overlayer on an alumina support, a vanadia overlayer on a silica support, vanadia overlayer on a tin oxide support, a tungsten oxide overlayer on a silica support, a niobia overlayer on a silica support, and a titania overlayer on a silica support.

5. The process of claim 1 wherein the bulk metal oxide catalyst is selected from the group consisting of molybdates (Mo), chromates (Cr), vanadates (V), rhenates (Re), titanates (Ti), niobates (Nb), manganates (Mn), tungstates (W) and mixtures thereof.

6. The process of claim 5 wherein the bulk metal oxide catalyst comprises at least one member selected from the group consisting of $PbV_2O_6$, $NaVO_3$, $Na_3VO_4$, $BiVO_4$, $AlVO_4$, $FeVO_4$, $Mg_3(VO_4)_2$, $Mg_2V_2O_7$, $CeVO_4$, $Zn_3(VO_4)_2$, $CdV_2O_7$, $Zn_2O_7$, $VOPO_4$, $KVO_3$, $Pb_2V_2O_7$, $TlVO_4$, $PbMoO_4$, $CaMoO_4$, $Bi_2Mo_2O_9$, $Bi_3(FeO_4)(MoO_4)_3$, $Na_2MoO_4$, $MnMoO_4$, $Gd_2(MoO_4)_3$, $MgMoO_4$, $CuMoO_4$, $CoMoO_4$, $Fe_2(MoO_4)_3$, $Te_2MoO_7$, $NiMoO_4$, $Al_2(MoO_4)_3$, $Cr_2(MoO_4)_3$, $Na_2Mo_2O_7$, $YNbO_4$, $YbNbO_4$, $LiNbO_3$, $NaNbO_3$, $KNbO_3$, $AlNbO_4$, $K_8Nb_6O_{19}$, $BiNbO_4$, $SbNbO_4$, $NbOPO_4$, $CaNb_2O_6$, $K_4Nb_6O_{17}$, $KCa_2Nb_3O_{10}$, $Li_6WO_6$, $FeWO_4$, $CoWO_4$, $MnWO_4$, $NiWO_4$, $CuWO_4$, $CaWO_4$, $Cs_2WO_4$, $Na_2WO_4$, $BaWO_4$, $Fe_2(WO_4)_3$, $Al_2(WO_4)_3$, $SrWO_4$, $K_2WO_4$, $Na_2W_2O_7$, $Li_2WO_4$, $CsLuW_2O_8$, $BiWO_4$, $MnAl_2O_4$, $KMnO_4$, $MnO$, $MnO_2$, $Mn_2O_3$, $Mn_3O_4$, $Na_2CrO_4$, $Na_2Cr_2O_7$, $Na_2Cr_3O_{10}$, $Na_2Cr_4O_{13}$, $K_2CrO_4$, $K_2Cr_2O_7$, $K_2Cr_3O_{10}$, $K_2Cr_4O_{13}$, $Fe_2(CrO_4)_3$, $CaCrO_4$, $Cs_2CrO_4$, $BiCrO_4$, $NaReO_4$, $Li_6ReO_4$, $Mg(ReO_4)_2$, $Na_2TiO_3$, $NaTiO_3$, $BaTiO_4$, and $BaTiO_3$.

7. The process of claim 1 wherein said contacting with the first catalyst is conducted at a temperature between 200° and 400° C. and said contacting with the second catalyst is conducted at a temperature between 200° and 700° C.

8. The process of claim 7 wherein said contacting with the first catalyst is conducted at a temperature between 250° and 350° C. and said contacting with the second catalyst is conducted at a temperature between 325° and 500° C.

9. The process of claim 8 wherein said gas containing said methyl mercaptan is contacted with said second catalyst such that between $10^{-2}$ and $10^4$ cubic centimeters of methyl mercaptan contacts a gram of catalyst per minute.

10. The process of claim 9 wherein between $10^{-1}$ and $10^2$ cubic centimeters of methyl mercaptan contact a gram of catalyst per minute.

11. The process of claim 1 wherein the methyl mercaptan is $CH_3SH$.

\* \* \* \* \*